United States Patent
Friebe et al.

(10) Patent No.: US 7,288,557 B2
(45) Date of Patent: Oct. 30, 2007

(54) TRIAZOLE DERIVATIVES

(75) Inventors: Walter-Gunar Friebe, Mannheim (DE); Ulrike Reiff, Penzberg (DE); Thomas von Hirschheydt, Penzberg (DE); Edgar Voss, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 163 days.

(21) Appl. No.: 11/226,677

(22) Filed: Sep. 14, 2005

(65) Prior Publication Data

US 2006/0211750 A1    Sep. 21, 2006

(30) Foreign Application Priority Data

Sep. 21, 2004   (EP) .................................. 04022371

(51) Int. Cl.
*A61K 31/422*  (2006.01)
*C07D 263/32*  (2006.01)
(52) U.S. Cl. ..................... 514/374; 548/235
(58) Field of Classification Search ................ 548/235; 514/374
See application file for complete search history.

(56) References Cited

FOREIGN PATENT DOCUMENTS

| EP | 1270571 | | 1/2003 |
|----|---------|---|--------|
| JP | WO03059907 | * | 1/2003 |
| WO | WO98/03505 | | 1/1998 |
| WO | WO 01/77107 | | 10/2001 |
| WO | WO 03/031442 | | 4/2003 |
| WO | WO 03/059907 | | 7/2003 |

OTHER PUBLICATIONS

Golub et al, Oct. 15, 1999, Science, 286, p. 531-537.*
Hortobagyi, G., Oct. 1, 1998, N. Engl., J. Med, 339, 974-984.*
Novak, Conference Report—Protein Kinase Inhibitors in Cancer Treatment: Mixing and Matching, Apr. 2004, MedGenMed, 6(2), p. 1-10, retrieved from <http://www.pubmedcentral.nih.gov/articlerender.fcgi?artid=1395807>.*
Wilks, A.F., Progress in Growth Factor Research, 2, pp. 97-111 (1990).
Chan et al., Cur. Opin. in Immunol., 8, pp. 394-401 (1995).
Yarden et al., Ann. Rev. Biochem., 57, pp. 443-478 (1988).
Wright et al., Br. J. Cancer, 65, pp. 118-121 (1992).
Baselga et al., Oncology, 63 (Suppl. 1), pp. 6-16 (2002).
Ranson et al., Oncology, 63 (Suppl. 1), pp. 17-24 (2002).
Bastin et al., Organic Proc. Res. Dev., 4, pp. 427-435 (2000).

* cited by examiner

*Primary Examiner*—Kamal A. Saeed
*Assistant Examiner*—Karen Cheng
(74) *Attorney, Agent, or Firm*—George W. Johnston; Patricia S. Rocha-Tramaloni; Gene J. Yao

(57) ABSTRACT

The present invention relates to the compounds of formula I

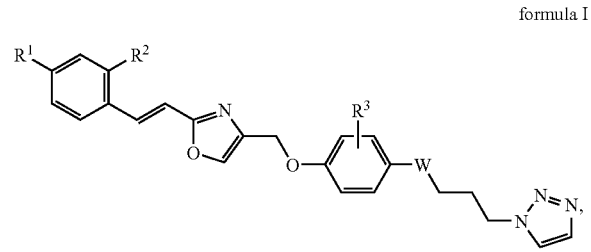

formula I their pharmaceutically acceptable salts or esters, enantiomeric forms, diastereoisomers and racemates, the preparation of the above-mentioned compounds, compositions containing such compounds and their manufacture, as well as the use of such compounds in the control or prevention of illnesses such as cancer.

17 Claims, No Drawings

TRIAZOLE DERIVATIVES

PRIORITY TO RELATED APPLICATIONS

This application claims the benefit of European Application No. 04022371.1, filed Sep. 21, 2004, which is hereby incorporated by reference in its entirety.

FIELD OF THE INVENTION

The present invention relates to novel triazole derivatives, to a process for their manufacture, pharmaceutical compositions containing them and their manufacture as well as the use of these compounds as pharmaceutically active agents.

BACKGROUND OF THE INVENTION

Protein tyrosine kinases (PTKs) catalyze the phosphorylation of tyrosyl residues in various proteins involved in the regulation of cell growth and differentiation (Wilks et al., Progress in Growth Factor Research 97 (1990) 2; Chan, A. C., and Shaw, A. S., Curr. Opin. Immunol. 8 (1996) 394-401). Such PTKs can be divided into receptor tyrosine kinases (e.g. EGFR/HER-1, c-erB2/HER-2, c-met, PDGFr, FGFr) and non-receptor tyrosine kinases (e.g. src, lck). It is known that many oncogenes encode proteins which are aberrant tyrosine kinases capable of causing cell transformation (Yarden, Y., and Ullrich, A., Annu. Rev. Biochem. 57 (1988) 443-478; Larsen et al., Ann. Reports in Med. Chem., 1989, Chpt. 13). Also over-expression of a normal proto-oncogenic tyrosine kinase may result in proliferative disorders.

It is known that receptor tyrosine kinases of the HER-family like HER-2 and EGFR (HER-1) are frequently aberrantly expressed in common human cancers such as breast cancer, gastrointestinal cancer (colon, rectal or stomach cancer), leukemia and ovarian, bronchial and pancreatic cancer. High levels of these receptors correlate with poor prognosis and response to treatment (Wright, C., et al., Br. J. Cancer 65 (1992) 118-121).

Accordingly, it has been recognized that inhibitors of receptor tyrosine kinases are useful as selective inhibitors of the growth of mammalian cancer cells. Therefore several small molecule compounds as well as monoclonal antibodies are in clinical trials for the treatment of various types of cancer (Baselga, J., and Hammond, L. A., Oncology 63 (Suppl. 1) (2002) 6-16; Ranson, M., and Sliwkowski, M. X., Oncology 63 (suppl. 1) (2002) 17-24).

Some substituted oxazoles are known in the art. WO 98/03505, EP 1 270 571, WO 01/77107, WO 03/031442 and WO 03/059907 disclose related heterocyclic compounds as tyrosine kinase inhibitors.

However there remains a need for new compounds with improved therapeutic properties, such as enhanced activity, decreased toxicity, better solubility and improved pharmacokinetic profile, to name only a few.

SUMMARY OF THE INVENTION

The present invention relates to compounds of general formula I and pharmaceutically acceptable salts or esters thereof wherein formula I is:

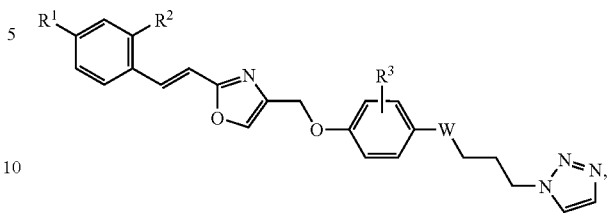

formula I wherein:
(a) $R^1$ is selected from the group consisting of:
  (1) —O-alkyl, wherein the alkyl group is optionally substituted with one or more halogens; and
  (2) —S-alkyl, wherein the alkyl group is optionally substituted with one or more halogens;
(b) $R^2$ is selected from the group consisting of:
  (1) hydrogen; and
  (2) halogen;
(c) $R^3$ is selected from the group consisting of:
  (1) hydrogen;
  (2) alkyl; and
  (3) halogen; and
(d) W is selected from the group consisting of:
  (1) —C(O)—;
  (2) —CH(OH)—; and
  (3) —C(alkyl)(OH)—.

The compounds of formula I are useful for preventing or treating proliferative diseases and conditions such as tumor growth and cancer including, but not limited to, breast cancer, leukemia, ovarian cancer, bronchial or lung cancer, pancreatic cancer, and gastrointestinal cancer such as colon cancer, rectal cancer, and stomach cancer.

The compounds of the present invention show activity as inhibitors of the HER-signaling pathway and therefore possess anti-proliferative activity. The present invention provides compounds of formula I and their pharmaceutically acceptable salts or esters, enantiomeric forms, diastereoisomers and racemates, the preparation of the above-mentioned compounds, compositions containing them and their manufacture as well as the use of the above-mentioned compounds in the control or prevention of illnesses, especially of illnesses and disorders as mentioned above like common human cancers (e.g. breast cancer, gastrointestinal cancer (colon, rectal or stomach cancer), leukemia and ovarian, bronchial and pancreatic cancer) or in the manufacture of corresponding pharmaceutical compositions.

DETAILED DESCRIPTION OF THE INVENTION

As used herein, the term "alkyl" means a saturated, straight-chain or branched-chain hydrocarbon containing from 1 to 4, preferably 1 or 2, carbon atoms. Examples are methyl, ethyl, n-propyl, isopropyl, n-butyl, 2-butyl, and t-butyl. If said alkyl group is substituted one or several times by halogen, it is substituted preferably by fluorine. Examples are difluoromethyl, trifluoromethyl, 2,2,2-trifluoroethyl, perfluoroethyl and the like.

As used herein, the term "halogen" means fluorine, chlorine, bromine or iodine, preferably fluorine, chlorine or bromine and more preferably fluorine or chlorine.

As used herein, when referring to the receptor tyrosine kinases of the HER-family like HER-2 and EGFR (HER-1), the acronym "HER" refers to human epidermal receptor and the acronym "EGFR" refers to epidermal growth factor receptor.

As used herein, "DMSO" refers to N,N-dimethylsulfoxide.

As used herein, the term "DMF" refers to N,N-dimethyl formamide.

As used herein, in relation to nuclear magnetic resonance (NMR) the term "$D_6$-DMSO" refers to deuterated N,N-dimethylsulfoxide.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The compounds according to the present invention may exist in the form of their pharmaceutically acceptable salts or esters. The term "pharmaceutically acceptable salt" refers to conventional acid-addition salts that retain the biological effectiveness and properties of the compounds of formula I and are formed from suitable non-toxic organic or inorganic acids. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See, e.g., Stahl, P. H., and Wermuth, G., (editors), Handbook of Pharmaceutical Salts, Verlag Helvetica Chimica Acta (VHCA), Zürich, (2002) or Bastin, R. J., et al., Organic Proc. Res. Dev. 4 (2000) 427-435.

Preferred are the pharmaceutically acceptable salts, which are formed with p-toluenesulfonic acid, naphthalenesulfonic acid, naphthalenedisulfonic acid, methanesulfonic acid and hydrochloric acid.

In a preferred embodiment, $R^1$ of formula I represents trifluoromethoxy or trifluoromethylsulfanyl, and in a further preferred embodiment, $R^1$ of formula I represents trifluoromethoxy.

In a preferred embodiment, the position of $R^3$ of formula I on the central phenyl ring is meta to the oxazolylmethoxy substituent.

An embodiment of the invention are the compounds of formula I, wherein $R^2$ is hydrogen and $R^3$ is hydrogen or alkyl.

Another embodiment of the invention are the compounds of formula I, wherein $R^2$ is hydrogen and $R^3$ is hydrogen.

Another embodiment of the invention are the compounds of formula I, wherein W is —C(O)—.

Another embodiment of the invention are the compounds of formula I, wherein:
  $R^2$ is hydrogen;
  $R^3$ is hydrogen or alkyl; and
  W is —C(O)—.

Still another embodiment of the invention are the compounds of formula I, wherein:
  $R^2$ is hydrogen;
  $R^3$ is hydrogen; and
  W is —C(O)—.

Still another embodiment of the invention are the compounds of formula I, wherein:
  $R^1$ is —O—$CF_3$, —O—$CHF_2$, or —S—$CF_3$; and
  W is —C(O)—.

Still another embodiment of the invention are the compounds of formula I, wherein:
  $R^1$ is —O—$CF_3$, —O—$CHF_2$, or —S—$CF_3$; and
  $R^2$ is hydrogen;
  $R^3$ is hydrogen or alkyl; and
  W is —C(O)—.

Still another embodiment of the invention are the compounds of formula I, wherein:
  $R^1$ is —O—$CF_3$, —O—$CHF_2$, or —S—$CF_3$;
  $R^2$ is hydrogen;
  $R^3$ is hydrogen; and
  W is —C(O)—.

For example, such compounds can be selected from the group consisting of:
4-[1,2,3]Triazol-1-yl-1-(4-{2-[2-(4-trifluoromethylsulfanyl-phenyl)-vinyl]-oxazol-4-ylmethoxy}-phenyl)-butan-1-ol; and
4-[1,2,3]Triazol-1-yl-1-(4-{2-[2-(4-trifluoromethoxy-phenyl)-vinyl]-oxazol-4-ylmethoxy}-phenyl)-butan-1-one.

Another embodiment of the invention are the compounds of formula I, wherein W is —CH(OH)—.

Another embodiment of the invention are the compounds of formula I, wherein:
  $R^2$ is hydrogen;
  $R^3$ is hydrogen or alkyl; and
  W is —CH(OH)—.

Another embodiment of the invention are the compounds of formula I, wherein:
  $R^2$ is hydrogen;
  $R^3$ is hydrogen; and
  W is —CH(OH)—.

Still another embodiment of the invention are the compounds of formula I, wherein:
  $R^1$ is —O—$CF_3$, —O—$CHF_2$, or —S—$CF_3$; and
  W is —CH(OH)—.

Still another embodiment of the invention are the compounds of formula I, wherein:
R¹ is —O—CF₃, —O—CHF₂, or —S—CF₃;
R² is hydrogen;
R³ is hydrogen or alkyl; and
W is —CH(OH)—.

Still another embodiment of the invention are the compounds of formula I, wherein:
R¹ is —O—CF₃, —O—CHF₂, or —S—CF₃;
R² is hydrogen;
R³ is hydrogen; and
W is —CH(OH)—.

Such a compound is for example, 4-[1,2,3]Triazol-1-yl-1-(4-{2-[2-(4-trifluoromethoxy-phenyl)-vinyl]-oxazol-4-yl-methoxy}-phenyl)-butan-1-ol Another embodiment of the invention are the compounds of formula I, wherein W is —C(alkyl) (OH)—.

Another embodiment of the invention are the compounds of formula I, wherein:
R² is hydrogen;
R³ is hydrogen or alkyl; and
W is —C(alkyl)(OH)—.

Another embodiment of the invention are the compounds of formula I, wherein:
R² is hydrogen;
R³ is hydrogen; and
W is —C(alkyl)(OH)—.

Still another embodiment of the invention are the compounds of formula I, wherein:
R¹ is —O—CF₃, —O—CHF₂, or —S—CF₃; and
W is —C(alkyl)(OH)—.

Still another embodiment of the invention are the compounds of formula I, wherein:
R¹ is —O—CF₃, —O—CHF₂, or —S—CF₃,
R² is hydrogen;
R³ is hydrogen or alkyl; and
W is —C(alkyl)(OH)—.

Still another embodiment of the invention are the compounds of formula I, wherein:
R¹ is —O—CF₃, —O—CHF₂, or —S—CF₃;
R² is hydrogen;
R³ is hydrogen; and
W is —C(alkyl)(OH)—.

Still another embodiment of the invention are the compounds of formula I, wherein:
R¹ is selected from the group consisting of:
(a) —O-alkyl substituted with one to five halogens, and
(b) —S-alkyl substituted with one to five halogens;
R² is hydrogen;
R³ is hydrogen; and
W is —C(O)— or —CH(OH)—.

In a more specific embodiment of the preceding above embodiment, R¹ is —O-alkyl, preferably substituted with one to three halogens and more preferably substituted by fluorine. In another specific embodiment of the preceding above embodiment, R¹ is —S-alkyl, preferably substituted with one to three halogens and more preferably substituted by fluorine.

Still another embodiment of the invention are the compounds of formula I, wherein:
R¹ is —O—CF₃ or —S—CF₃;
R² is hydrogen;
R³ is hydrogen; and
W is —C(O)— or —CH(OH)—.

Still another embodiment of the invention is a process for the manufacture of the compounds of formula I, wherein:
(a) the compound of formula V:

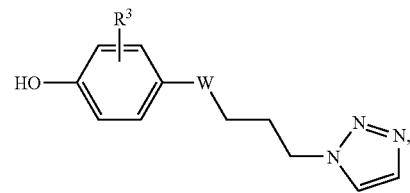

formula V wherein R³ has the significance as given in formula I above and W is —C(O)—, is reacted with a compound of formula VI:

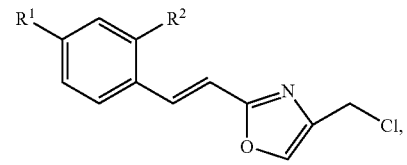

formula VI wherein R¹ and R² have the significance given in formula I above, to give the respective compound of formula Ia:

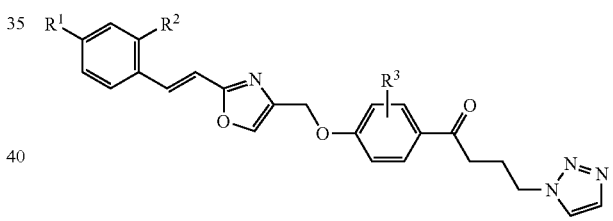

formula Ia (b) optionally, the compound of formula Ia is reduced to give the respective compound of formula Ib:

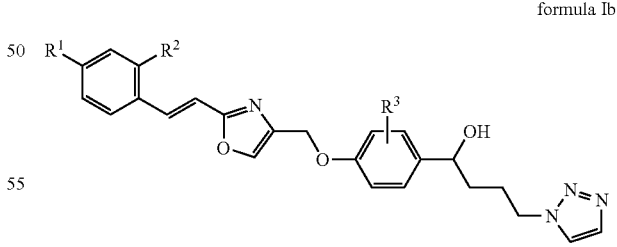

formula Ib (c) optionally said compound of formula Ia or Ib is isolated from the reaction mixture, and
(d) optionally converted into a pharmaceutically acceptable salt or ester.

The derivatives of the general formula I or a pharmaceutically acceptable salt or ester thereof, may be prepared by any process known to be applicable for the preparation of chemically-related compounds by the one skilled in the art.

Such processes, when used to prepare the triazole derivatives of formula I, or a pharmaceutically-acceptable salt or ester thereof, are provided as a further feature of the invention and are illustrated by the following representative examples of scheme 1, in which, unless otherwise stated $R^1$, $R^2$ and $R^3$ have the significance given herein before. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

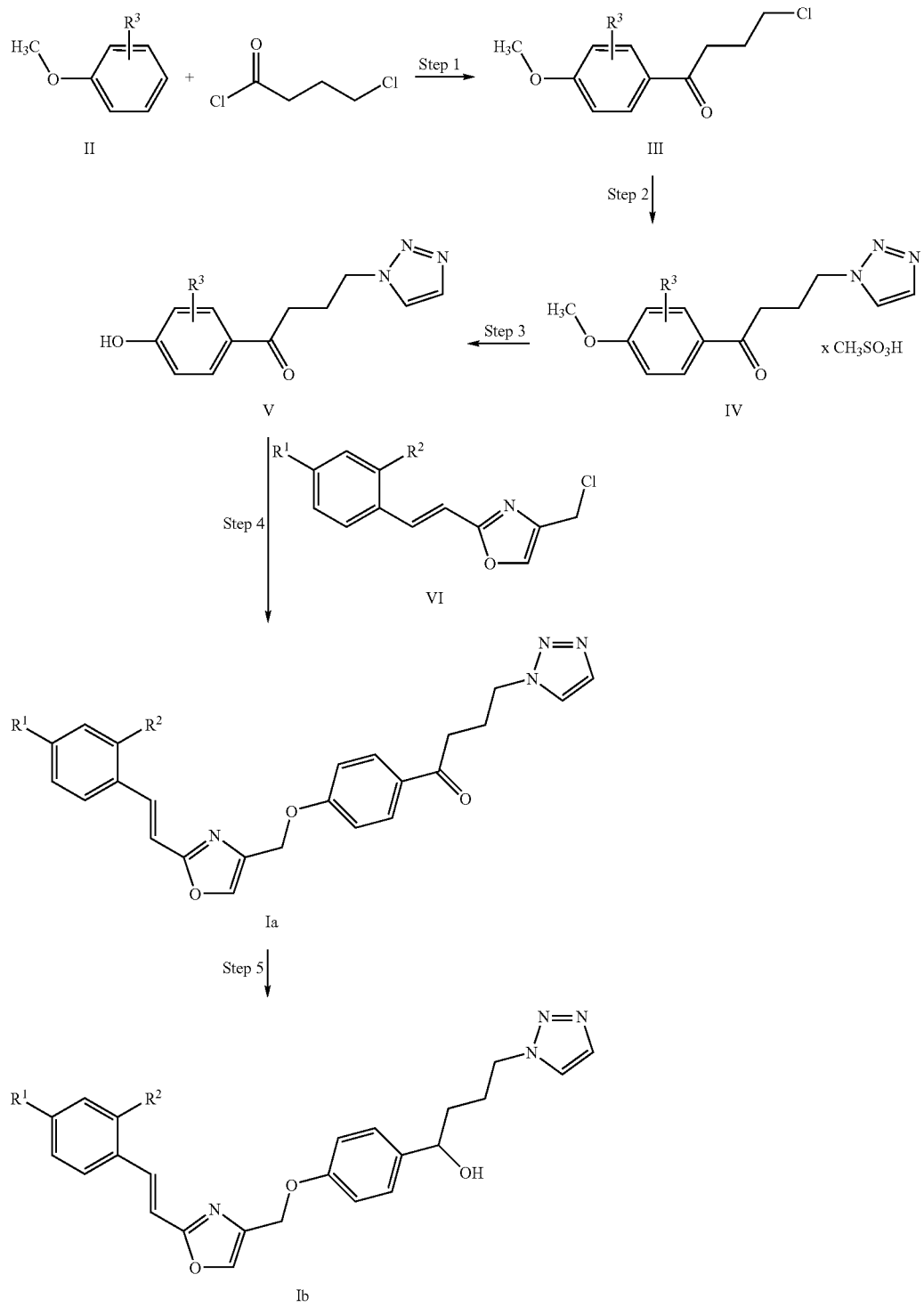

Step 1 of scheme 1 represents a standard Friedel-Crafts acylation of the anisoles of formula II with 4-chloro-butyryl chloride. The reaction is typically carried out with Lewis acid catalysts like $AlCl_3$, $AlBr_3$ or the like in inert solvents like toluene, tetrahydrofuran (THF) or the like.

Step 2 is a N-alkylation reaction of triazole with the chlorides of formula III. Typically such alkylation is carried out in solvents like DMF, methanol, ethanol and isopropanol. Typical bases for this reaction are alkaline carbonates, sodium methylate, sodium hydride or lithium diisopropyl amide. The reaction temperatures may vary from 20° C. to 150° C. Other preferred alkylation procedures make use of alkaline carbonates as bases in solvents like ketones, for example cesium carbonate in 2-butanone at reflux temperature, or sodium hydride in DMF at room temperature.

In Step 3 of scheme 1 the anisole ethers of formula IV are cleaved to release the corresponding phenolic derivatives of formula V. Typically this reaction is carried out with HBr in water or acetic acid under heating. Alternatively HI or other Lewis acids like $BF_3$, $BCl_3$, $Me_2BBr$, $Me_3SiI$ and the like can be used for the ether cleavage.

The derivatives of formula I wherein W is —C(O)— are named Ia and can be obtained by reactions well known to someone skilled in the art, e.g. by alkylation of compounds of formula V with compounds of formula VI according to Step 4 scheme 1. The alkylation can be carried out in the presence of potassium iodide or sodium iodide in solvents like DMF, methanol, ethanol, isopropanol and 2-butanone. Typical bases for this reaction are sodium methylate, sodium hydride, lithium diisopropyl amide or cesium carbonate. The reaction temperatures may vary from 50° C. to 150° C.

The derivatives of formula I wherein W is —CH(OH)— are named Ib and can be obtained by reduction of the corresponding ketones of formula Ia. Typically sodium borohydride, diisobutylaluminium hydride (DIBAL) or other reducing reagents are used.

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

The compounds of formula I and their pharmaceutically acceptable salts or esters possess valuable pharmacological properties. It has been found that said compounds inhibit the HER-signalling pathway and show anti-proliferative activity. Consequently the compounds of the present invention are useful in the therapy and/or prevention of illnesses with known over-expression of receptor tyrosine kinases of the HER-family like HER-2 and EGFR (HER-1), especially in the therapy and/or prevention of illnesses mentioned above. The activity of the present compounds as HER-signalling pathway inhibitors is demonstrated by the following biological assay:

Viability Assay of HEK293 Cells

A viability assay was performed using the CellTiter-Glo® Luminescent Cell Viability Assay (see Promega Corporation's Technical No. 288, pp. 1-11 [revised February 2004] which is hereby incorporated by reference in its entirety). This assay is a homogeneous method of determining the number of viable cells in culture based on quantitation of the ATP present, an indicator of metabolically active cells. The assay is designed for use with multiwell formats, making it ideal for automated high-throughput screening (HTS), cell proliferation and cytotoxicity assays. The homogeneous assay procedure involves adding a single reagent (containing luciferase, luciferan substrate, and buffer) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The above-referenced assay generates a "glow-type" luminescent signal, produced by the luciferase reaction, which has a half-life generally greater than five hours, depending on cell type and medium used. The extended half-life eliminates the need to use reagent injectors and provides flexibility for continuous or batch mode processing of multiple plates. The unique homogeneous format avoids errors that may be introduced by other ATP measurement methods that require multiple steps.

HEK293 cells (human embryonic kidney cell line transformed by Adenovirus 5 fragments, ATCC-No. CRL 1573) were cultivated in Dulbecco's Modified Eagle Medium (D-MEM) (1×) liquid (high glucose) (which includes L-Alanyl-L-Glutamine [a stabilized a form of L-Glutamine], 4500 mg/L glucose, and 110 mg/L sodium pyruvate) from Invitrogen Corporation (Invitrogen Catalog Number 31966-021 [now 10569-010] which is hereby incorporated by reference in its entirety), 5% Fetal Calf Serum (FCS, Sigma Cat-No. F4135 [FBS] which is hereby incorporated by reference in its entirety), and 100 Units/ml penicillin/100 µg/ml streptomycin (=Pen/Strep from Invitrogen Cat. No. 15140, which is hereby incorporated by reference in its entirety). For the assay the cells were seeded in 384 well plates, 5000 cells per well, in the same medium. The next day the test compounds were added in various concentrations ranging from 3 µM to 0.00015 µM (10 concentrations, 1:3 diluted). After 7 days the above viability assay was performed in accordance with the following steps:

Step 1: The cell-plate was equilibrated to room temperature for approximately 30 minutes and than the assay reagent (containing luciferase, luciferan substrate, and buffer) was added.

Step 2: The contents were carefully mixed for 15 minutes to induce cell lysis.

Step 3: After 45 minutes the luminescent signal was measured in Victor 2, (scanning multiwell spectrophotometer, Wallac).

Details:

$1^{st}$ Day:

Medium: Dulbecco's Modified Eagle Medium (D-MEM) (1×) liquid (high glucose) (which includes L-Alanyl-L-Glutamine [a stabilized a form/source of L-Glutamine], 4500 mg/L glucose, and 110 mg/L sodium pyruvate) from Invitrogen Corporation (Invitrogen Catalog Number 31966-021 [now 10569-010]), 5% Fetal Calf Serum (FCS, Sigma Cat-No. F4135 [FBS]), and Pen/Strep containing 100 Units/ml penicillin/100 µg/ml streptomycin (Invitrogen Catalog Number 15140).

HEK293 (ATCC-No. CRL 1573): 5000 cells in 60 µl per well of 384 well plate (Greiner 781098, white plates) Incubate 24 h at 37° C., 5% $CO_2$.

2nd day: Induction (Substance Testing):

In general the dilution steps are 1:3
a) Add 8 µl of 10 mM stock solution of compound to 72 µl DMSO
b) dilute 9×1:3 (always 30 µl to 60 µl DMSO) in this DMSO dilution row (results in 10 wells with concentrations from 1000 µM to 0.06 µM)
c) dilute each concentration 1:4.8 (10 µl compound dilution to 38 µl medium)
d) dilute each concentration 1:10 (10 µl compound dilution to 90 µl medium)
e) add 10 µl of every concentration to 60 µl medium in the cell plate
   resulting in final concentration of DMSO:0.3% in every well
   and resulting in final concentration of compounds from 3 µM to 0.00015 µM
   Incubate 168 h (7 days) at 37° C., 5% $CO_2$
   Analysis:
   Add 30 µl of reagent cited above (containing luciferase, luciferan substrate, and buffer),
   shake 15 minutes at room temperature
   incubate further 45 minutes at room temperature without shaking.
   Measurement:
   Victor 2 scanning multiwell spectrophotometer (Wallac), Luminescence mode
   Determine IC50 by curve fitting using XLfit® software (ID Business Solution Ltd., Guilford, Surrey, UK) which his hereby incorporated by reference in its entirety.

With all compounds a significant inhibition of HEK293 cell viability was detected, which is exemplified by the compounds shown in Table 1. The reference compound as used herein is 4-[1,2,3]Triazol-1-yl-1-(4-{2-[2-(4-trifluoromethyl-phenyl)-vinyl]-oxazol-4-ylmethoxy}-phenyl)-butan-1-one (Example 42, p. 148, WO 03/059907).

TABLE 1

Results

| Examples | IC50 HEK293 [nM] |
|---|---|
| Reference compound | 164 |
| 1 | 17.9 |
| 2 | 21.1 |
| 3 | 29.9 |

In Vivo Assay on Tumor Inhibition:

To generate primary tumors, Non-Small-Cell Lung Cancer (NSCLC) (e.g. Calu-3 (ATTC HTB-55) or A549 (ATTC CCL-185)) cells (4-5.0×10$^6$ in a volume of 100 µl) are injected subcutaneously into the left flank of female SCID beige mice (Severe Combined Immunodeficient/beige mice available from Charles River, Sulzfeld, Germany) or BALB/c nude mice (BALB/c Nude Spontaneous Mutant Mice (homozygotes) available from Taconic Europe, Ry, Denmark). The cells are thawed and expanded in vitro before use in the experiment. Mice are assigned to the treatment groups 14-21 days after cell injection. For grouping (n=10-15 mice per group), the animals are randomized to get a similar mean primary tumor volume of ca. 100-150 mm$^3$ per group. The test compounds are administered orally once per day as a suspension in 7.5% gelatine 0.22% NaCl with an administration volume of 10 ml/kg based on actual body weights. Treatment is initiated one day after staging, and carried out until day 20-50, the final day of the study. The subcutaneous primary tumors are measured twice weekly, starting prior to randomisation, in two dimensions (length and width) using an electronic caliper. The volume of the primary tumor is calculated using the formula: V[mm$^3$]=(length [mm]×width [mm]×width [mm])/2. In addition, the body weight of all animals is recorded at least twice weekly. Finally, at the end of the study the tumors are explanted and weighed.

The compounds according to this invention and their pharmaceutically acceptable salts or esters can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. For example, lactose, corn starch or derivatives thereof, talc, stearic acids or it's salts and the like can be used as carriers for tablets, coated tablets, dragées and hard gelatine capsules. Suitable carriers for soft gelatine capsules are, for example, vegetable oils, waxes, fats, semi-solid and liquid polyols and the like. However, depending on the nature of the active substance, carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions may comprise, for example, the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG (direct tab letting grade) | 125 | 105 | 30 | 150 |
| 3. | Sta-Rx 1500 (pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|------|-------------|------|------|------|------|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Micro Suspension
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 μm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenize.

The above described preparation yields micro-suspensions of the compounds of formula I with particle sizes between 1 and 10 μm. The suspensions are suitable for oral applications and can be used in the in vivo assay described above.

Pharmaceutical compositions containing a compound of the present invention or a pharmaceutically acceptable salt or ester thereof and a therapeutically inert carrier are also an object of the present invention, as is a process for their production, which comprises bringing one or more compounds of the present invention and/or pharmaceutically acceptable salts or esters and, if desired, one or more other therapeutically valuable substances into a galenical administration form together with one or more therapeutically inert carriers.

In accordance with the invention the compounds of the present invention as well as their pharmaceutically acceptable salts or esters are useful in the control or prevention of illnesses. Based on their HER-signalling pathway inhibition and their antiproliferative activity, said compounds are useful for the treatment of diseases such as cancer in humans or animals and for the production of corresponding pharmaceutical compositions. The dosage depends on various factors such as the manner of administration, species, age and/or individual state of health.

Another embodiment of the invention is a pharmaceutical composition, containing one or more compounds of formula I together with pharmaceutically acceptable excipients.

Still another embodiment of the invention is said pharmaceutical composition for the inhibition of tumor growth.

Still another embodiment of the invention is the use of a compound of formula I for the treatment of cancer.

Still another embodiment of the invention is the use of a compound of formula I for the manufacture of corresponding pharmaceutical compositions for the inhibition of tumor growth.

The following examples and references are provided to aid the understanding of the present invention, the true scope of which is set forth in the appended claims. It is understood that modifications can be made in the procedures set forth without departing from the spirit of the invention.

EXAMPLES

Example 1

4-[1,2,3]Triazol-1-yl-1-(4-{2-[(E)-2-(4-trifluoromethoxy-phenyl)-vinyl]-oxazol-4-ylmethoxy}-phenyl)-butan-1-one

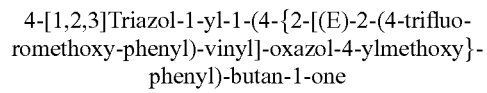

To a cooled solution of 10.8 g (0.1 mol) anisole in 100 ml anhydrous toluene 13.3 g (0.1 mol) aluminium trichloride was added in portions over 15 minutes at −10° C. then 15.5 g (12.3 ml, 0.1 mmol) 4-chloro-butyryl chloride were added over 15 minutes keeping the temperature at −10° C. After stirring for additional 30 minutes at −10° C. the reaction mixture was hydrolyzed and the layers were separated. The aqueous layer was extracted with toluene (three times 100 ml) and the combined organic layers were dried and evaporated to yield 20.8 g (97%) 4-chloro-1-(4-methoxy-phenyl)-butan-1-one as a light beige liquid that solidified on standing. The product was used without further purification.

$^1$H-NMR (400 MHz, D$_6$-DMSO): δ=2.06 (quintet, 2H); 3.12 (t, 2H); 3.71 (t, 2H); 3.85 (s, 3H); 7.05 (d, 2H); 7.95 (d, 2H).

10.6 g (50 mmol) 4-Chloro-1-(4-methoxy-phenyl)-butan-1-one, 20 ml 2-methyl-2-butanol, 5.2 g (75 mmol) 1H-[1,2,3]-triazole, 9.5 g (57 mmol) potassium iodide and 3.0 g (75 mmol) NaOH were stirred at 100° C. for 4 h. After removal of solvents in vacuo, the residue was partitioned between toluene and water. Washing of the toluene phase twice with water, drying over sodium sulphate and evaporation gave an oily residue that was dissolved in 80 ml diisopropyl ether/ethyl acetate (1:2). The solution was kept at 20° C. during the addition of 2.8 ml methanesulfonic acid and stirred at room temperature for 2 h. The formed precipitate was isolated, washed with cold diethyl ether and dried at 40° C. in vacuo to give 1-(4-methoxy-phenyl)-4-[1,2,3]triazol-1-yl-butan-1-one methanesulfonate. Yield: 2.25 g (13%).

$^1$H-NMR (400 MHz, D$_6$-DMSO): δ=2.16 (quintet, 2H); 2.45 (s, 3H); 3.00 (t, 2H); 3.84 (s, 3H); 4.46 (t, 2H); 7.04 (d, 2H); 7.76 (s, 1H); 7.92 (d, 2H); 8.19 (s, 1H).

1.70 g (5.0 mmol) 1-(4-Methoxy-phenyl)-4-[1,2,3]triazol-1-yl-butan-1-one methane-sulfonate and 7 ml 47% aqueous HBr were heated to 80° C. overnight. After diluting with 10 ml water and cooling to 0° C. the mixture was alkalized (pH 12.6) by dropwise addition of 4N NaOH and extracted three times with toluene. Concentration of the toluene phase in vacuo gave 0.05 g recovered starting material. The aqueous phase was cooled and adjusted to pH=6.3 by addition of 6 N HCl. The resulting precipitate was isolated and dried in vacuo at 40° C. to give 1-(4-hydroxy-phenyl)-4-[1,2,3]triazol-1-yl-butan-1-one. Yield: 0.96 g (83%).

$^1$H-NMR (400 MHz, D$_6$-DMSO): δ=2.14 (quintet, 2H); 2.94 (t, 2H); 4.45 (t, 2H); 6.85 (d, 2H); 7.73 (s, 1H); 7.82 (d, 2H); 8.16 (s, 1H); 10.34 (s, 1H).

To a solution of 116 mg (0.5 mmol) 1-(4-hydroxy-phenyl)-4-[1,2,3]triazol-1-yl-butan-1-one in 10 ml 2-butanone 98 mg (0.3 mmol) cesium carbonate was added and the mixture was stirred at 60° C. for 30 minutes. Then 152 mg (0.5 mmol) 4-chloromethyl-2-[(E)-2-(4-trifluoromethoxy-phenyl)-vinyl]-oxazole and 83 mg (0.5 mmol) potassium iodide were added and the mixture was stirred at 60° C. overnight. After removal of all volatiles in vacuo the residue was purified by column chromatography on silica (ethyl acetate) to give 4-[1,2,3]triazol-1-yl-1-(4-{2-[(E)-2-(4-trifluoromethoxy-phenyl)-vinyl]-oxazol-4-ylmethoxy}-phenyl)-butan-1-one. Yield: 200 mg (81%) white solid.

$^1$H-NMR (400 MHz, D$_6$-DMSO): δ=2.16 (quintet, 2H); 3.00 (t, 2H); 4.46 (t, 2H); 5.14 (s, 2H); 7.16 (d, 2H); 7.22 (d, J=16.2 Hz, 1H); 7.41 (d, 2H); 7.58 (d, J=16.2 Hz, 1H); 7.73 (s, 1H); 7.87 (d, 2H); 7.93 (d, 2H); 8.17 (s, 1H); 8.27 (s, 1H).

Example 2

(rac)-4-[1,2,3]Triazol-1-yl-1-(4-{2-[(E)-2-(4-trifluoro-methoxyphenyl)-vinyl]-oxazol-4-ylmethoxy}-phenyl)-butan-1-ol To a solution of 10 mg (0.26 mmol) sodium borohydride in 10 ml methanol 100 mg (0.20 mmol) 4-[1,2,3]triazol-1-yl-1-(4-{2-[(E)-2-(4-trifluoromethoxy-phenyl)-vinyl]-oxazol-4-ylmethoxy}-phenyl)-butan-1-one were added in portions and the mixture was stirred at room temperature overnight. The reaction was monitored by thin layer chromatography (silica/ethyl acetate R$_f$=0.27) and an additional amount of 10 mg sodium borohydride was added and stirring was continued for 3 hours to complete the reaction. After removal of all volatiles in vacuo 20 ml water were added to the residue and the mixture was extracted with diethyl ether (three times 15 ml). The combined organic layers were dried over sodium sulfate and evaporated to dryness. Yield: 97 mg (97%) white solid.

$^1$H-NMR (400 MHz, D$_6$-DMSO): δ=1.41-1.61 (m, 2H); 1.69-1.95 (m, 2H); 4.37 (t, 2H); 4.45-4.55 (t, 1H); 4.99 (s, 2H); 5.14 (d, J=4.5 Hz, 1H); 6.97 (d, 2H); 7.21 (d, J=16.2 Hz, 1H); 7.22 (d, 2H); 7.41 (d, 2H); 7.57 (d, J=16.2 Hz, 1H); 7.69 (s, 1H); 7.87 (d, 2H); 8.09 (s, 1H); 8.21 (s, 1H).

Example 3

4-[1,2,3]Triazol-1-yl-1-(4-{2-[(E)-2-(4-trifluoromethylsulfanyl-phenyl)-vinyl]-oxazol-4-ylmethoxy}-phenyl)-butan-1-one 4-[1,2,3]Triazol-1-yl-1-(4-{2-[(E)-2-(4-trifluoromethylsulfanyl-phenyl)-vinyl]-oxazol-4-ylmethoxy}-phenyl)-butan-1-one was prepared analogously to example 1.

$^1$H-NMR (400 MHz. D$_6$-DMSO): δ=2.16 (quintet, 2H); 3.00 (t, 2H); 4.46 (t, 2H); 5.14 (s, 2H); 7.16 (d, 2H); 7.31 (d, J=16.2 Hz, 1H); 7.59 (d, J=16.2 Hz, 1H); 7.73 (s, 1H); 7.34 (d, 2H); 7.88 (d, 2H); 7.93 (d, 2H); 8.17 (s, 1H); 8.29 (s, 1H).

Unless stated to the contrary, all compounds in the examples were prepared and characterized as described. All ranges recited herein encompass all combinations and sub-combinations included within that range limit. All patents and publications cited herein are hereby incorporated by reference in their entirety.

The invention claimed is:

1. A compound of formula I or pharmaceutically acceptable salts or esters thereof wherein formula I is:

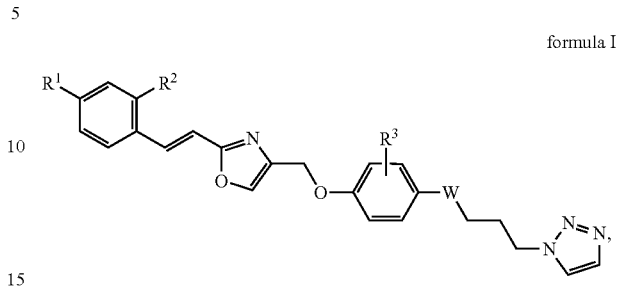

formula I wherein:
(a) R$^1$ is selected from the group consisting of:
 (1) —O-alkyl; wherein the alkyl group is optionally substituted with one or more halogens; and
 (2) —S-alkyl; wherein the alkyl group is optionally substituted with one or more halogens;
(b) R$^2$ is selected from the group consisting of hydrogen and halogen;
(c) R$^3$ is selected from the group consisting of hydrogen, alkyl and halogen; and
(d) W is selected from the group consisting of —C(O)—, —CH(OH)— and —C(alkyl)(OH)—.

2. The compounds according to claim 1, wherein:
(a) R$^2$ is hydrogen; and
(b) R$^3$ is selected from the group consisting of hydrogen and alkyl.

3. The compounds according to claim 1, wherein:
(a) R$^2$ is hydrogen; and
(b) R$^3$ is hydrogen.

4. The compounds according to claim 1, wherein:
(a) R$^1$ is selected from the group consisting of —O—CF$_3$, —O—CHF$_2$, and —S—CF$_3$; and
(b) W is —C(O)—.

5. The compounds according to claim 4, wherein:
(a) R$^2$ is hydrogen; and
(b) R$^3$ is selected from the group consisting of hydrogen and alkyl.

6. The compounds according to claim 1, wherein:
(a) R$^1$ is selected from the group consisting of —O—CF$_3$, —O—CHF$_2$, and —S—CF$_3$; and
(b) W is —CH(OH)—.

7. The compounds according to claim 6 wherein:
(a) R$^2$ is hydrogen; and
(b) R$^3$ is selected from the group consisting of hydrogen and alkyl.

8. The compounds according to claim 1, wherein W is —C(alkyl) (OH)—.

9. The compounds according to claim 1, wherein W is —C(O)—.

10. The compounds according to claim 1, wherein W is —CH(OH)—.

11. The compounds according to claim 1 selected from the group consisting of:
(a) 4-[1,2,3]Triazol-1-yl-1-(4-{2-[2-(4-trifluoromethylsulfanyl-phenyl)-vinyl]-oxazol-4-ylmethoxy}-phenyl)-butan-1-ol;

(b) 4-[1,2,3]Triazol-1-yl-1-(4-{2-[2-(4-trifluoromethoxy-phenyl)-vinyl]-oxazol-4-ylmethoxy}-phenyl)-butan-1-one; and
(c) 4-[1,2,3]Triazol-1-yl-1-(4-{2-[2-(4-trifluoromethoxy-phenyl)-vinyl]-oxazol-4-ylmethoxy}-phenyl)-butan-1-ol.

12. A process for the manufacture of compounds of formula I in claim 1, wherein:
(a) the compound of formula V:

formula V

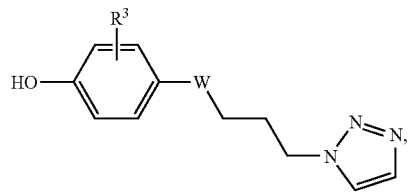

wherein:
$R^3$ is selected from the group consisting of hydrogen, alkyl and halogen; and wherein
W is —C(O)—, is (b) reacted with a compound of formula VI formula VI

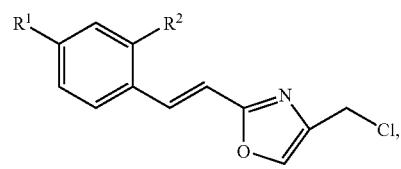

wherein:
$R^1$ is selected from the group consisting of:
(1) —O-alkyl; wherein the alkyl group is optionally substituted with one or more halogens; and
(2) —S-alkyl; wherein the alkyl group is optionally substituted with one or more halogens; and wherein $R^2$ is selected from the group consisting of hydrogen and halogen; to give the respective compound of formula Ia;

formula Ia

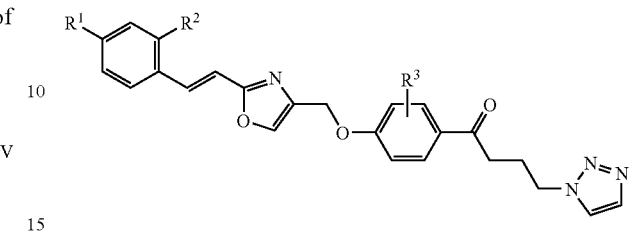

wherein $R^1$, $R^2$, and $R^3$ are defined the same as above.

13. A process according to claim 12, further comprising the step of reducing the compound of formula Ia to give the respective compound of formula Ib:

formula Ib

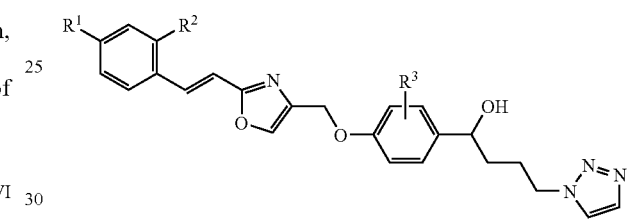

wherein $R^1$, $R^2$ and $R^3$ are defined according to claim 7.

14. A process according to claim 12, further comprising isolating formula Ia from the reaction mixture.

15. A process according to claim 13, further comprising isolating formula Ib from the reaction mixture.

16. A process according to claim 12, further comprising converting formula Ia into a pharmaceutically acceptable salt or ester.

17. A process according to claim 13, further comprising converting formula Ib into a pharmaceutically acceptable salt or ester.

* * * * *